United States Patent [19]

Nishiyama

[11] Patent Number: 5,093,940
[45] Date of Patent: Mar. 10, 1992

[54] LENS EXCHANGEABLE GOGGLE

[76] Inventor: Takashi Nishiyama, No. 22-4 Eharacho 1-Chome, Nakano-Ku, Tokyo, Japan

[21] Appl. No.: 649,532

[22] Filed: Feb. 1, 1991

[51] Int. Cl.⁵ ............................................. A61F 9/02
[52] U.S. Cl. ................................... 2/441; 2/440; 351/43
[58] Field of Search ............ 2/431, 438, 439, 440, 2/441, 443, 430, 428; 351/43, 47, 59

[56] References Cited

U.S. PATENT DOCUMENTS

| | | | |
|---|---|---|---|
| 2,364,584 | 12/1944 | Malcom | 2/440 |
| 2,846,684 | 8/1958 | Hill | 2/438 |
| 3,229,303 | 1/1966 | Jonassen | 351/47 |
| 3,944,345 | 3/1976 | Decorato | 351/43 |
| 4,051,557 | 10/1977 | Bengtson et al. | 351/43 |
| 4,229,837 | 10/1980 | Solari | 2/431 |
| 4,286,340 | 9/1981 | Lathrop | 2/430 |
| 4,367,561 | 1/1983 | Solari | 2/439 |
| 4,468,819 | 9/1984 | Ohno | 351/43 |
| 4,689,838 | 9/1987 | Angermann et al. | 2/441 |

FOREIGN PATENT DOCUMENTS 1004403 2/1977 Canada ............................... 2/440

Primary Examiner—Werner H. Schroeder
Assistant Examiner—Michael A. Neas
Attorney, Agent, or Firm—Cushman, Darby & Cushman

[57] ABSTRACT

A lens exchangeable goggle having adjustable distance and/or fixing angle of lens units which includes as components a lens unit having a tubular portion, a opening formed with a wider width than the lens unit in a mask frame and a holding mechanism for fixing detachably the lens unit.

6 Claims, 5 Drawing Sheets

LENS EXCHANGEABLE GOGGLE

FIELD OF THE INVENTION

This invention relates to a goggle with detachable and/or replaceable lenses.

DESCRIPTION OF THE PRIOR ART

There are two types of goggles, that is, monocular and binocular goggles. To insert the lens into positions of the left and right eyes, the binocular type of goggle is selected for use. This binocular type goggle is designed so that the optical axis of lens can be aligned to the center of eye, even when the compensation of vision is not intended. For this purpose, it is known a goggle constructed so that the distance between the left-hand and right-hand lens is adjustable to the interpupillary distance of both eyes (Japanese Utility Model KOKAI No. 182322/1984).

The conventional type goggles are composed separately of both left-hand and right-hand lens, and these lenses are connected by an intermediate joint which adjusts the distance between them. That joint is made from a soft synthetic resin which allows elastic deformation in connecting and detaching of the lens. This results in a defect which makes it difficult to fix or detach the lens and to adjust the interpupillary distance. Since the joint and its connecting edge is very small and they lack enough strength, there is a problem of chipping at the connecting edge and the joint is lost frequently during the manufacture or use. Further, there are problems of increased manufacturing steps and poor yield because various consideration is needed for design of a mold for the goggle so as to allow its transfer of the position of lenses. Although the binocular type of goggle is constructed to allow for compensation of vision, a combination of the lens portion, joint and belt with one another will cause difficulties in handling. This invention is aimed at solving the above mentioned problems and defects.

SUMMARY OF THE INVENTION

It is an object of this invention to provide an lens exchangeable goggle of the binocular type, in which the fixing distance between a pair of lens units can be adjusted without using a joint and the adjustment of distance is easily done without causing any damage, and lens units are easy to fix and detach.

The above mentioned object of this invention has been attained with a lens exchangeable goggle which comprises a mask frame having a pair of openings in right and left positions of the mask frame and a pair of lens units inserted in said openings, in which each of said lens units is composed of a spectacle lens, a tubular portion formed around the spectacle lens and a collar portion projecting outwardly from backside of the tubular portion; each of said openings in said mask frame is formed with a wider width in right and left than the width of backside of the tubular portion of the lens unit so as the distance between the lens units and/or fixing angle of lens unit are adjustable; and upper and lower external edges of the tubular portion of each of the lens units are interlocked with internal edge of each of the openings by means of a holding mechanism so as to hold detachably and moveably the lens unit in the opening of the mask frame.

By virtue of the invention, such variations of the basic design have been developed as goggles for swimming, skiing, motorcycling and other sports, sunglasses, general purpose goggles and safety goggles.

DETAILED DESCRIPTION OF THE PREFERRED EMBODIMENTS

In the following paragraphs, this invention will be described in detail by reference to the drawings.

FIG. 1 is an embodiment of the goggle. This type of goggle has a lens opening (21) for inserting respectively the lens units (10) in the right and left positions of the mask frame (20). The distance between the center of both the right and left lens openings (21) and (22) can be adjusted to fit the center of the average distance between the eyes.

Figure 3:
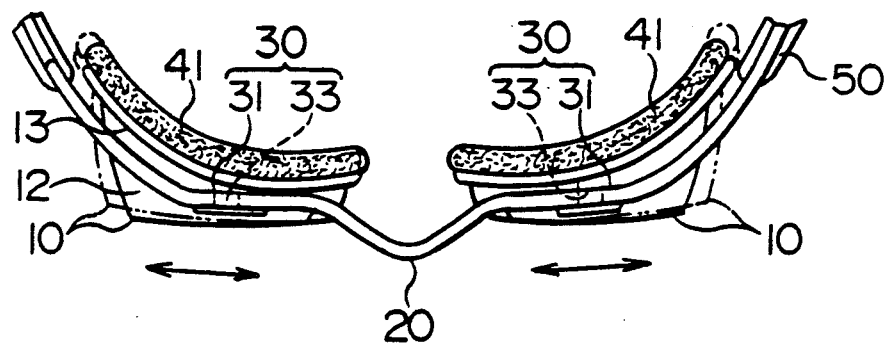
Figure 4:
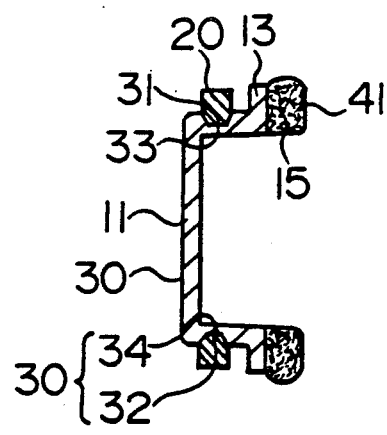
FIG. 4 and FIG. 5 are cross-sectional views of lens units.
Figure 5:
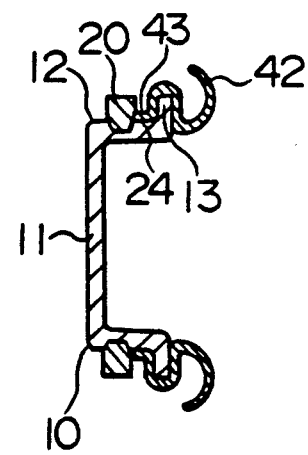

The lens unit (10) is composed of three parts: spectacle lens (11); tubular portion (12) formed around the spectacle lens; and collar portion (13) which projects outwardly from backside of the tubular portion. The external side of tubular portion (12) is formed to be longer in the front and back directions than the internal side so that the wearer's line of view can intersect with the spectacle lens (11) at any desired angle (See FIG. 3).

The mask frame (20) is used to insert the lens unit (10) into the lens opening (21) from the backside (or the inside) of the mask frame to hold the lens unit at the tubular portion (12) and collar portion (13) tightly. With a holding mechanism locked in place, it is possible to shift the lens unit (10) left and right. The width of the lens opening (21) is formed to be wider in right and left than the width of backside of tubular portion (12). On the central upper and lower edges of the lens opening (21), the moving portions (22) and (23) are provided so that the lens unit can be moved either right or left. The moving portions are composed of parallel straight lines or substantially parallel curves.

The holding mechanism (30) locks the lens unit (10) in the frame (20) while allowing the lens unit (10) to be easily movable and detachable. The embodiment shown in FIG. 1 is composed of the following parts: concave channels (31) and (32) which are located on the upper and lower edges of the tubular portion (12), and the projections (33) and (34) which are located at the upper and lower edges of opening (21) in the mask frame (20). The projections (33) and (34) are designed to come into contact with the concave channels (31) and (32) so that the lens units are able to rotate slightly round a hypothetical fixing axis.

On the backside of the lens unit (10), an ocular mechanism is attached. Its suitable components are the ringshaped ocular pad (41) made of a spongy synthetic resin such as urethane or neoprene rubber or the ocular seal (42) made of transparent silicone rubber. The ocular pad is bonded on the backside surface (15) of the collar portion (13). The ocular seal (42) is attached to cover circumference of the collar portion (13). Although both of the ocular mechanisms can be watertight, the ocular seal (42) is best suited for swimming goggles. For the ocular seal (42), it is possible to furnish the lip (43), which is fixed on tubular portion (12) by means of the edge (24) of the lens opening (21).

To illustrate the method of wearing the goggles, the elastic strap (50) is shown in the figures. This elastic strap (50) has a pair of T-shaped hooks (51) on the left and right edges of the mask frame (20). Other embodiments of the means of wearing adoptable for the goggles are eye seat materials which are identical with what is called arms on the eyeglass frame.

Figure 1A:
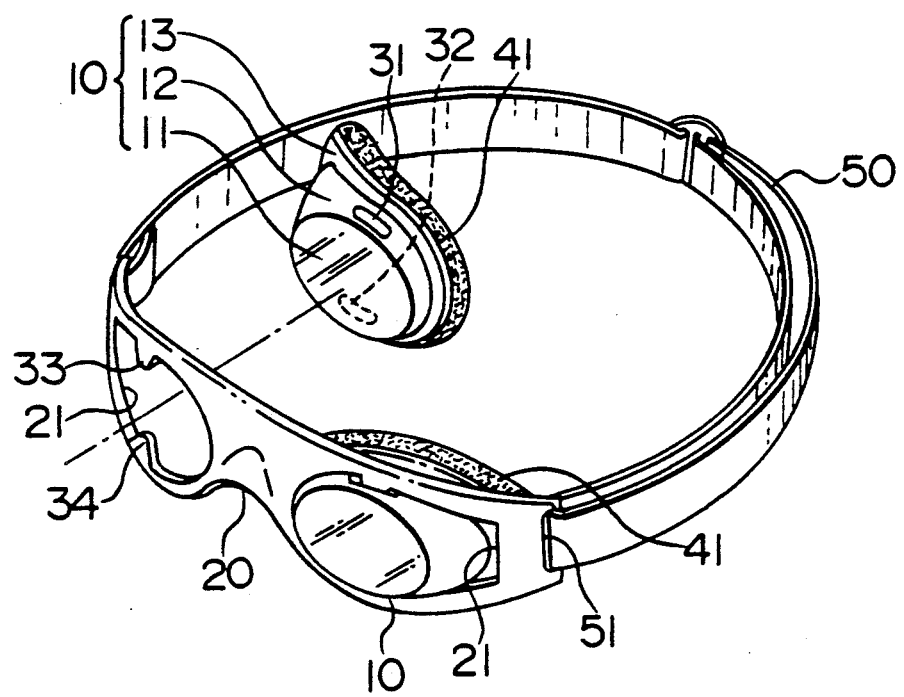
FIG. 1A is an oblique view of a goggle with a lens unit shown in FIG. 1B.
Figure 1B:
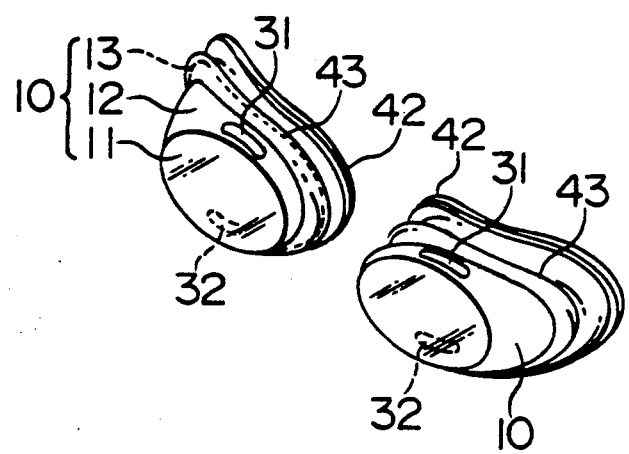
Figure 2:
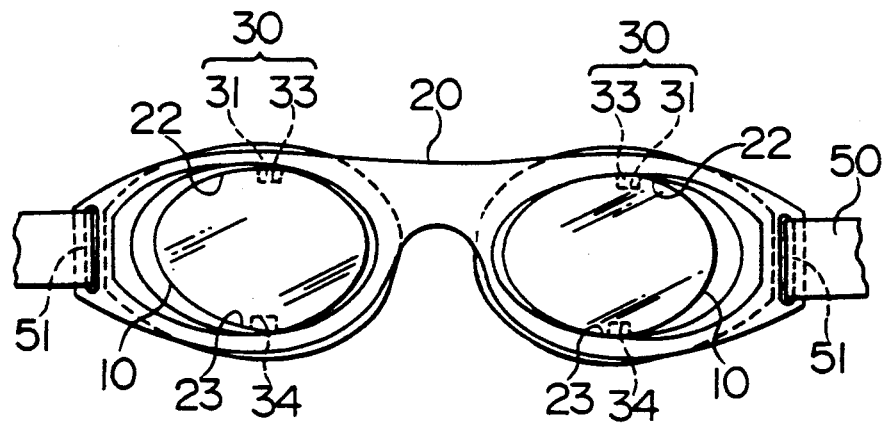
FIG. 2 is a front view and FIG. 3 is a top view of the goggle with lens units.
Figure 6A:
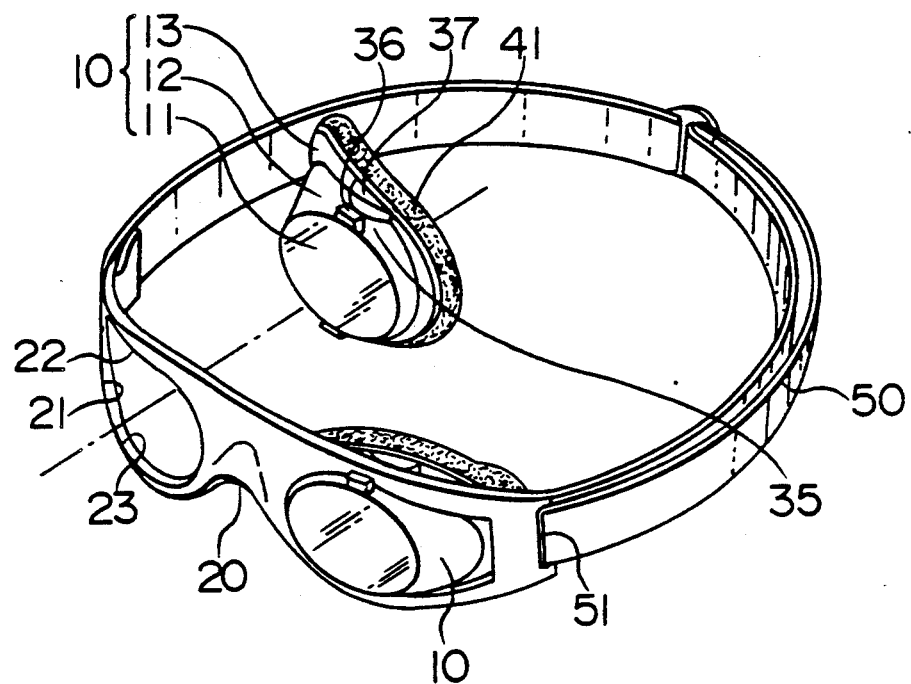
FIG. 6A is an oblique view of another goggle with a lens unit shown in FIG. 6B.
Figure 6B:
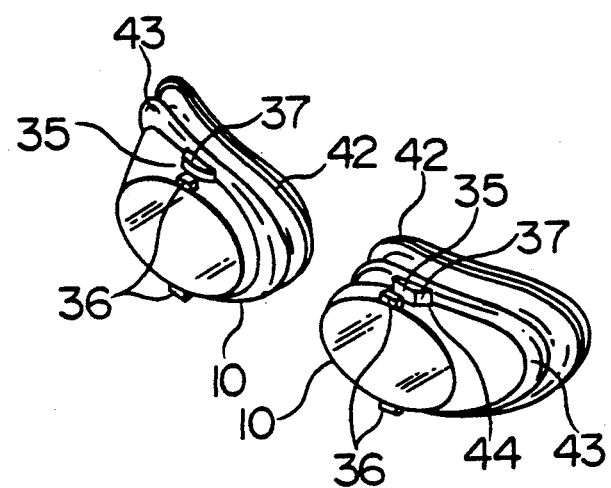
Figure 7:
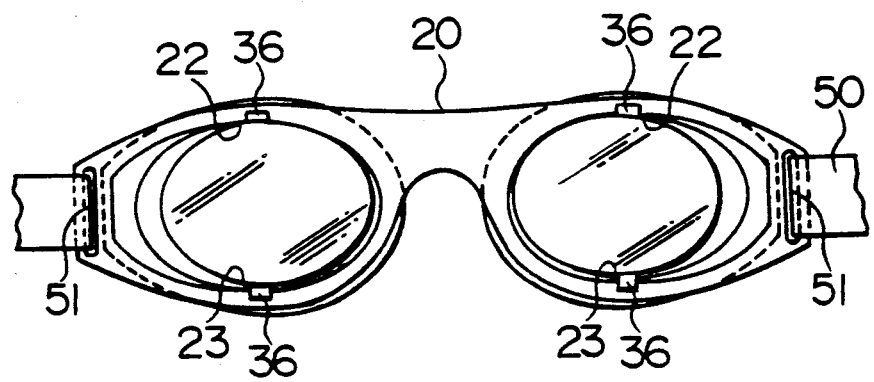
FIG. 7 is a front view and FIG. 8 is a top view of the goggle with lens units.
Figure 8:
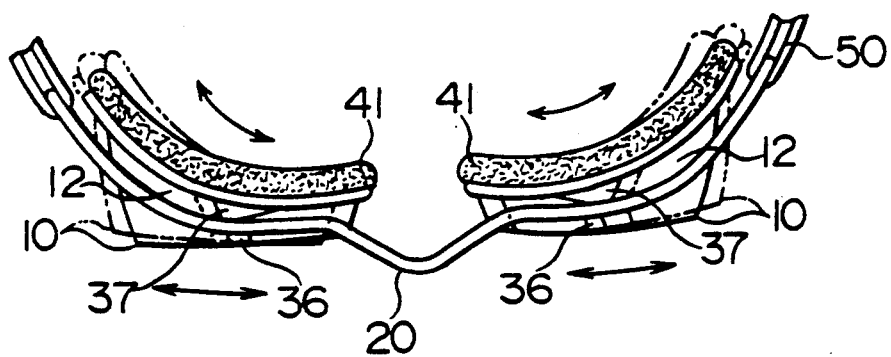
Figure 9:
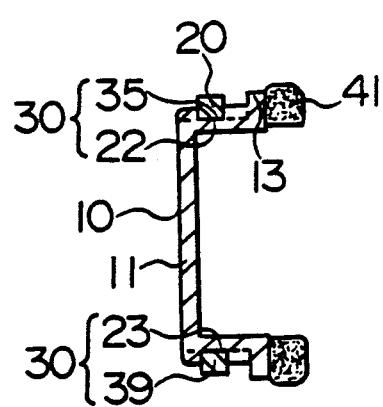
FIG. 9 and FIG. 10 are cross-sectional views of lens units.
Figure 10:
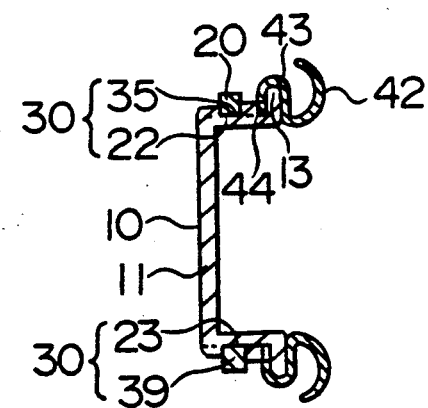

An embodiment of the goggle shown in FIG. 6 will be illustrated hereunder: the lens unit (10), which is made up of the spectacle lens (11), the tubular portion (12), and the collar portion (13) in the same way as the embodiment shown in FIG. 1, is furnished with an engaging portion (35) as a means of the holding mechanism (30), and no special structure is provided on the mask frame (20). It is constructed so as the moving portions (22) and (23) on the lens opening (21) can contact with the engaging portion (35). The engaging portion (35) is composed of a pair of projections (36) and (37) on each of the upper and lower external surfaces of the tubular portion, which are extruded from the tubular portion (12) at approximately the same position as the concave channels (31) and (32). The back projection (37) stretches against the collar portion (13) and prevents the collar portion (13) from coming into contact with the back surface of the mask frame. It is in the shape of a trapezoid. The front projection (36) is a smaller trapezoid than the back projection (37). Since other structures are the same as those of the embodiment shown in FIGS. 1A and 1B, the description of the other affixed structures is omitted. When the ocular seal (42) is selected for the ocular mechanism of the lens unit (10), the cut-out (44) can be furnished so that the back projection (37) is not covered by the seal. In this case, the lip (43) of the ocular seal (42) will not be fixed on the mask frame (20), but comes into contact with the collar portion (13) (See FIG. 10).

In the embodiment in FIG. 6A, the spectacle lens (10) can move right and left in the way as shown in the embodiment in FIG. 1A. The lens unit (10) and the mask frame (20) are fixed and positioned to keep the distance between them by the amount of length equivalent to the thickness of the back projection (37) so that they can rotate more easily around a hypothetical axis.

Figure 11:
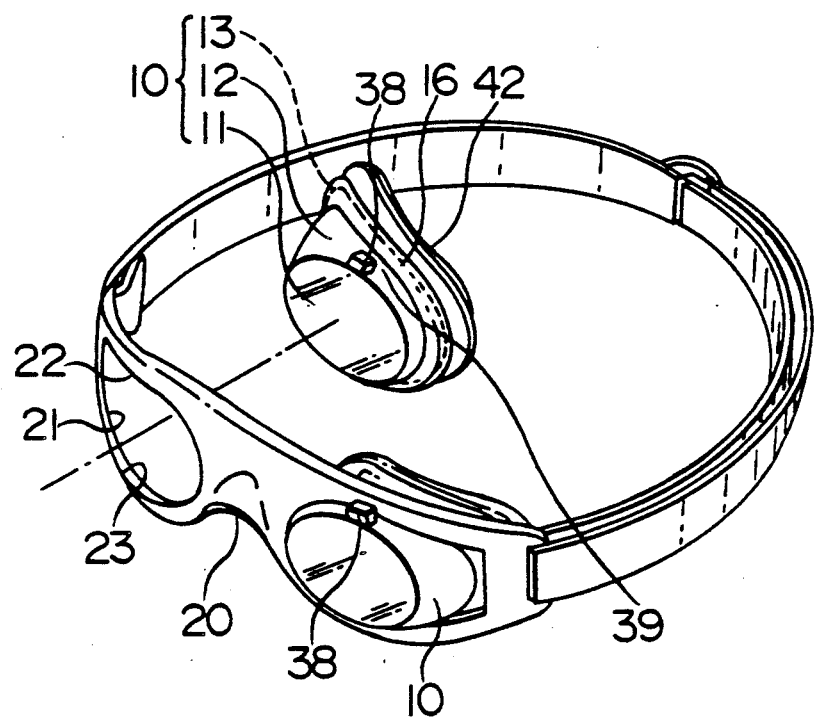
FIG. 11 is an oblique view of still another goggle with a lens unit.
Figure 12:
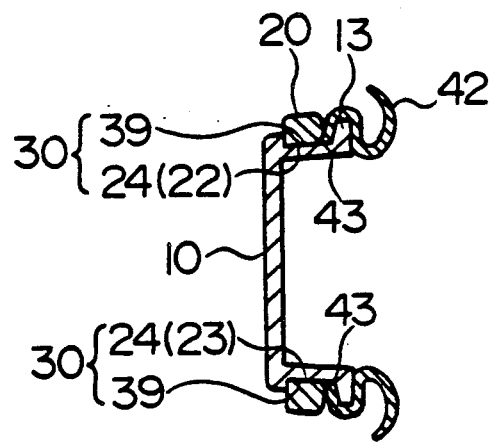
FIG. 12 and FIG. 13 are cross-sectional views of lens units.
Figure 13:
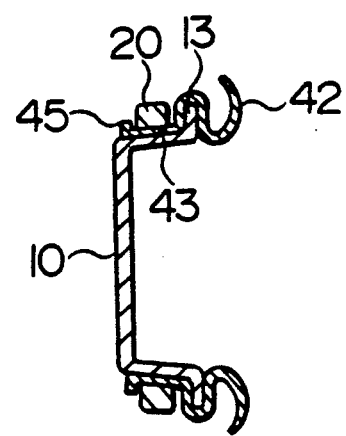

The embodiment shown in FIG. 11 illustrates that the concave engaging portion is used as the holding mechanism (30) and is defined by the front surface (16) of the collar portion (13) for the lens unit and the projection (38) located on the external surface of the tubular portion. The front surface (16) of the collar portion can come into contact with the back surface of the mask frame (20). In order for the lens unit (10) to rotate around a hypothetical axis, the structure is designed so that the width of the engaging portion (39) is slightly wider than the thickness of the engagement on the lens openings (21) of the mask frame and allowance is given to the engagement. The description of the other structures is the same as that of the example shown in FIGS. 1A and 1B. When the ocular seal (42) is used as the ocular mechanism for the lens unit (10), the projection (38) can be covered by the front extension of the surface by the opening edge (24) of the lens openings (21), and opening edge (24) is locked by the bead portion (45) which is provided at the front part of the lip (43).

Both the lens unit (10) and the mask frame (20) can be manufactured by method for forming synthetic resin. The lens unit (10) can be formed by hard resin materials. When the lens unit (11) is combined with the tubular portion (12), suitable materials are cellulose acetate (CA), cellulose propionate (CP), cellulose acetate butylate (CAB) and others including PS, PMMA, PET, polyamide resin, acrylic acid resin. A choice of selection is left to determine whether the color of those materials is chromatized or colored transparent. The spectacle lens (11) can be formed by a combination of concave and convex lenses to facilitate focusing. Furthermore, the mask frame (20) can be constructed in various colors and shapes. The suitable materials for the mask frame are a strong resin, synthetic or natural rubber including fiber reinforced rubber and metals.

The goggle comes with the following components: a pair of lens units (10) which are located side by side, right and left in the mask frame (20); lens opening (21) for inserting the lens unit (10) into the mask frame (20); hooks (51) which are located on the left and right of the left and right edges of the mask frame (20); and a head band which is inserted into the hooks (51). When assembling a pair of goggles, each pair of the lens units (10) is inserted from the backside (or inside) of the mask frame (20) into the lens opening (21) including the tubular portion (12) and the obstacle lens (10), and is fixed by the engaging mechanism (30) in the position of the mask frame (20). After that, the lens unit (10) can move left and right within the range of the moving portion (22) and (23). The distance between both lens unit (10) is fixed in the mask frame (20) and can be adjusted to fit the wearer's eyes. The ocular surface of the lens unit (10) can also be adjusted to fit the face of the wearer because the lens unit can rotate around a hypothetical axis. Because of this, attaching and detaching the lens unit (10), as well as adjusting the distance, can be done while the lens unit (10) and the mask frame (20) come into contact with each other.

The meritorious effects of this goggle are that the distance between the attached lens units can be adjusted without using a joint, and each lens unit can be adjusted to fit the face of the wearer. Additionally, these adjustments are easily done, and attaching and detaching the lens unit are also easily done.

I claim:

1. A lens exchangeable goggle which comprises a mask frame having a pair of openings in right and left positions of the mask frame and a pair of lens units inserted in said openings, in which each of said lens units is composed of a spectacle lens, a tubular portion formed around the spectacle lens and a collar portion projecting outwardly from the backside of the tubular portion; each of said openings in said mask frame is formed with a wider width in right and left than the width of the backside of the tubular portion of the lens unit; and upper and lower external edges of the tubular portion of each of the lens units are interlocked with internal edge of each of the openings by means of a holding mechanism so as to hold detachably and moveably the lens unit in the opening of the mask frame.

2. A lens exchangeable goggle according to claim 1, in which the openings in right and left positions of the mask frame are formed with parallel lines or substantially parallel curves stretching in right and left directions at the upper and lower edges of the openings.

3. A lens exchangeable goggle according to claim 1 or 2, in which the holding mechanism comprises concave channels provided on upper and lower external edges of the tubular portion of the lens unit, and projections provided at the upper and lower edges of the opening of the mask frame to be interlocked with the concave channels.

4. A lens exchangeable goggle according to claim 2, in which the holding mechanism comprises a pair of projections forming a gap between the pair of projections on each of the upper and lower external surfaces of the tubular portion, so as the gaps are interlocked with the edges of parallel lines or substantially parallel curves formed on the upper and lower edges of the opening.

5. A lens exchangeable goggle according to claim 2, in which the holding mechanism comprises a projection provided on each of upper and lower external surfaces of the tubular portion of the lens unit forming a gap between the projection and the front surface of the collar portion of the lens unit, so as the gaps are interlocked with edges of the parallel lines or substantially parallel curves formed on the upper and lower edges of the opening.

6. A lens exchangeable goggle according to claim 1, in which is provided in the backside of each of the lens units with an ocular seal comprising a lip to be caught and held between the tubular portion of the lens unit and an internal edge of the opening.

* * * * *